United States Patent
Thorpe

(10) Patent No.: US 10,321,916 B2
(45) Date of Patent: Jun. 18, 2019

(54) ELASTIC TOURNIQUET CAPABLE OF INFINITELY ADJUSTABLE COMPRESSION

(76) Inventor: Patricia E. Thorpe, Scottsdale, AZ (US)

(*) Notice: Subject to any disclaimer, the term of this patent is extended or adjusted under 35 U.S.C. 154(b) by 0 days.

(21) Appl. No.: 13/252,122

(22) Filed: Oct. 3, 2011

(65) Prior Publication Data

US 2012/0310273 A1   Dec. 6, 2012

Related U.S. Application Data

(63) Continuation-in-part of application No. 11/955,806, filed on Dec. 13, 2007, now abandoned, which is a continuation-in-part of application No. 11/940,225, filed on Nov. 14, 2007, now abandoned.

(60) Provisional application No. 60/901,715, filed on Feb. 13, 2007, provisional application No. 60/875,087, filed on Dec. 13, 2006.

(51) Int. Cl.
    *A61B 17/132*     (2006.01)
(52) U.S. Cl.
    CPC ................ *A61B 17/1322* (2013.01)
(58) Field of Classification Search
    CPC . A61B 17/1322; A61B 18/00; A61B 18/0003; A61B 18/0011; A61B 18/0023; A61B 18/0034
    USPC .............. 606/201–204, 157; 602/16, 44, 76; 24/170, 198, 200, 445; 442/184, 442/190–191; 57/203, 210, 225; 139/391, 393, 395; 428/91, 92, 100
    See application file for complete search history.

(56) References Cited

U.S. PATENT DOCUMENTS

| | | | |
|---|---|---|---|
| 658,539 A | 9/1900 | Baker | |
| 3,017,847 A * | 1/1962 | Rollin | ............................ 28/159 |
| 3,965,703 A | 6/1976 | Barnhardt | |
| 4,665,909 A | 5/1987 | Trainor | |
| 4,705,710 A * | 11/1987 | Matsuda | ......................... 428/92 |
| 5,120,300 A * | 6/1992 | Shaw | .............................. 602/61 |
| 5,140,718 A * | 8/1992 | Toth | ............................ 15/210.1 |
| 5,429,555 A | 7/1995 | Beckh | |
| 5,974,635 A * | 11/1999 | Murasaki | ........... A44B 18/0011 24/442 |
| 6,573,419 B2 * | 6/2003 | Naimer | ............... A61F 13/0273 602/41 |
| 6,845,639 B1 * | 1/2005 | Hajek | ................ A44B 18/0034 66/195 |
| 2003/0124277 A1 * | 7/2003 | Agarwal | ................... A61F 7/02 428/35.2 |

(Continued)

OTHER PUBLICATIONS

Walters, Thomas J. et al, Techncal Report, Laboratory Evaluation of Battlefield Tourniquets in Human Volunteers, United States Army Institute of Surgical Research, Sep. 2005.

(Continued)

*Primary Examiner* — Martin T Ton

(57) ABSTRACT

A tourniquet band is made of an elastic material and has a plush surface on one side and a series of hook fastener material patches on the reverse side. The woven structure includes a series of parallel elastic threads covered by a dense yet loosely coiled bundle of non-elastic threads. The non-elastic threads are oriented to form the plush surface while allowing the elastic core thread to elongate for applying pressure to a body part by elastic compression when the tourniquet is wrapped around the body part and secured by joining the hook material with the plush surface.

11 Claims, 2 Drawing Sheets

(56) References Cited

U.S. PATENT DOCUMENTS

2006/0189914 A1\* 8/2006 Slavitt .................. A61F 13/065
   602/75
2006/0253150 A1 11/2006 McEwen
2007/0072739 A1\* 3/2007 Kaufman ............ A61H 1/0285
   482/44
2008/0193709 A1\* 8/2008 Han ....................... B29C 70/10
   428/100
2009/0076432 A1\* 3/2009 Winkler .......................... 602/76
2009/0143709 A1\* 6/2009 Naumann ............. A61F 13/145
   602/44
2010/0042034 A1\* 2/2010 Riesinger ....................... 602/44

OTHER PUBLICATIONS

Walters, Thomas J. & Mabry, Robert L., Issues Related to the Use of Tourniquets on the Battlefield, Miltary Medicine, vol. 170, Sep. 2005.

\* cited by examiner

ELASTIC TOURNIQUET CAPABLE OF INFINITELY ADJUSTABLE COMPRESSION

CROSS-REFERENCE TO RELATED APPLICATIONS

This application is a continuation-in-part application of co-pending U.S. patent application Ser. No. 11/955,806, filed Dec. 13, 2007, which is a continuation-in-part application of U.S. patent application Ser. No. 11/940,225, filed Nov. 14, 2007, which is a continuation-in-part application of U.S. provisional patent application No. 60/901,715, filed Feb. 13, 2007, and a continuation-in-part of U.S. provisional patent Application No. 60/875,087, filed Dec. 13, 2006, the full disclosure of each of which applications are incorporated herein in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM USING COMPACT DISC APPENDIX

Not Applicable

BACKGROUND OF THE INVENTION

This disclosure relates to the field of athletic and medical wraps in general and specifically to a tourniquet for use with major vascular trauma. A tourniquet is a constricting or compressing device used to control venous and arterial circulation to an extremity for a period of time. Pressure is applied circumferentially upon the skin and underlying tissues of a limb; this pressure is transferred to the walls of vessels, causing them to become temporarily occluded. It is generally used as a tool for a medical professional in applications such as phlebotomy or to stem the flow of traumatic bleeding, especially by military medics.

The ideal tourniquet is applied quickly and effectively and controls hemorrhage with minimal risk of tissue damage. Potential complications of tourniquets include ischemia, thrombosis and nerve injury and compartment syndrome. Problems related to putting the tourniquet in place include device malfunction, mal-positioning, inadequate bleeding control or excessive pressure leading to continued hemorrhage or ischemia and nerve palsy respectively. Taking into account that soldiers, under extreme stress, have to apply the tourniquet to their own body or that of a comrade, the tourniquet should be fast, simple, not confusing and reliable. Since control of bleeding often requires two tourniquets, they should be light weight and easily accessed from a pocket or pack. Since many wounds require pressure dressings, the tourniquet may serve as a quick and effective means of securing gauze and packing in a scenario where tape doesn't work.

Surgical tourniquets prevent blood flow to a limb and enable surgeons to work in a bloodless operating field. This allows surgical procedures to be performed with improved precision, safety and speed. Tourniquets are widely used in orthopedic and plastic surgery, as well as in intravenous regional anesthesia where they serve the additional function of preventing local anesthetic in the limb from entering general circulation. Emergency tourniquets are used in emergency bleeding control to prevent severe blood loss from limb trauma. Emergency tourniquets are generally used as a last resort, especially in civilian applications, for if blood flow below the application of an emergency tourniquet is stopped, it can irreversibly compromise the tissue, leading to eventual loss of the limb below the tourniquet. However, use of tourniquets is widespread in military applications, and have the potential to save lives. Analysis has shown that in cases of major limb trauma, there is no apparent link between tourniquet application and morbidity of the limb. In recent years there have been significant advancements in tourniquets. These advancements have vastly improved tourniquet safety. Limb occlusion pressure (LOP) is the minimum tourniquet pressure required to occlude blood flow to a specific patient's limb at a specific time and accounts for a patient's limb and vessel characteristics, and the type and fit of the cuff. LOP can be determined by gradually increasing tourniquet pressure until distal arterial pulses cease, as indicated by a device sensing blood flow, such as a Doppler stethoscope. Studies have shown that cuff pressure based on LOP measured immediately prior to surgery is generally lower than commonly used cuff pressures and is sufficient to maintain a satisfactory surgical field. Automatic tourniquet systems are capable of providing safety features that are not possible in older mechanical tourniquets. These systems can monitor the cuff inflation time as well as regulate the cuff pressure to a known pressure throughout the surgical procedure. Some microprocessor controlled tourniquets are capable of calculating the proper pressure to ensure complete blood occlusion in about 30 seconds. This assists the operating room staff in deciding what the tourniquet pressure should be set at on a per-patient basis. Studies have shown that tourniquet cuff pressure can be substantially reduced by using wide, contoured cuffs. A wider and contoured cuff has more contact with the limb's surface area so it disperses the cuffs force. This concept is emerging from the surgical field into the emergency field with wider emergency tourniquets.

The Combat Application Tourniquet (CAT) was developed by Composite Resources, Inc. and is used by the U.S. and British military to provide soldiers a small, effective tourniquet in field combat situations, and is also in use by NHS ambulance services, and some UK fire and rescue services. The unit utilizes a windlass with a locking mechanism and can be self-applied. The CAT has been adopted by military and emergency personnel around the world. The present conflicts in Iraq and Afghanistan have demonstrated the value of timely and judicious use of tourniquets in the battle field and in field medical facilities with regard to saving limbs as well as the survival of those who have been injured. The above disclosed Combat Application Tourniquet technology and know-how, although widely implemented, has significant and serious limitations, such as being too complex for a dazed person to quickly affix and too expensive to manufacture.

BRIEF SUMMARY OF THE INVENTION

The presently disclosed apparatus is a greatly improved tourniquet fabricated as a single elongate fabric band with two opposing free ends, a smooth side and a fuzzy side with these surfaces common over the full length of the band. The band is elastically stretchable to about 150% of its relaxed length when under longitudinal tension. Bonded or otherwise attached to the smooth side of the band are patches of hook material, one at each of the ends of the band and one or more medially positioned. The hook material is able to latch onto the fuzzy finish so as to secure the band as wrapped around a limb while applying any selected hoop stress by stretching the band. The following advantages of the band are noted.

The band is of simple construction thereby being inexpensive to manufacture. It is extremely easy and simple to apply as a tourniquet. It is easily tightened to a desired compression force and also easily relaxed and later tightened again in cycles. It is able to be folded for compact storage as for instance to be carried in a pocket of a uniform. It is longitudinally symmetrical so that there is no distinction as to if it is applied starting from either one of its ends. It may be applied with equal results with either of its sides facing the subject body part. It is infinitely adjustable for achieving any compression force desired within the range of the band's capacity. It is made of durable material so that it may be reused many times and will last indefinitely.

In one embodiment, the tourniquet comprises a band of elastic and flexible material, having a width and a length, a first end and a second end, and a first face and second face, where at least a portion of the first face comprises hook-type fastener means located within a third of the band at the first end, within a third of the band at the second end, and within a middle third of the band, and where the second face comprises loop-type fastener means spanning the length of the second face.

In one preferred aspect, the band is applied across a body party, such as an appendage, head, neck or torso, the band being adapted to encircle the body part bidirectionally. As the band is extended from its first end to encircle the body part, the loop-type fastener means of the second face engages the hook-type fastener means of the first face, which may be at the second end, where the body part has a large diameter, or, more typically, at the middle third of the tourniquet.

Where the band has engaged at the middle third, the tourniquet is further extended from its second end to encircle the body part, and the loop-type fastener means of the second face engage the hook-type fastener means of the first face at the first end previously attached over the middle portion. The pressure potential of the tourniquet to curtail bleeding is significantly increased with the additional hook and loop attachment where the application of the tourniquet comprises the loop-type fastener means of the second face at the first end being engaged with the hook-type fastener means of the middle third of the first face, and the loop-type fastener means of the second face of the second end being engaged with the hook-type fastener means of the first face at the first end.

With the tourniquet, a method for impeding blood flow to a body part can be utilized by applying the tourniquet to compress a vessel at a region to stop bleeding and also may partially decrease blood flow to tissue supplied below that region. The method comprises applying a tourniquet comprising a band comprised of an elastic and flexible material, the band having a width and a length, a first end and a second end, and a first face and second face, where at least a portion of the first face comprises hook-type fastener means located within a third of the band at the first end, within a third of the band at the second end, and within a middle third of the band, and where the second face comprises loop-type fastener means spanning the length of the second face, whereby the band is adapted to encircle the body part bidirectionally. The tourniquet is applied at a specific region by extending the band from its first end to encircle the body part, whereby the loop-type fastener means of the second face engages the hook-type fastener means of the first face and subsequently extending the band from its second end to encircle the body part, in the opposite direction, whereby the loop-type fastener means of the second face engage the hook-type fastener means of the first face, securely enough that blood flow is decreased to tissue below the region.

In a preferred such method the loop-type fastener means of the second face of the tourniquet at the first end engages the hook-type fastener means of the middle third of the first face, and then the loop-type fastener means of the second face at the second end engages the hook-type fastener means of the first face at the first end.

The details of one or more embodiments of these concepts are set forth in the accompanying drawings and the description below. Other features, objects, and advantages will be apparent from the following description and drawings, and from the claims.

BRIEF DESCRIPTION OF THE SEVERAL VIEWS OF THE DRAWING

Like reference symbols in the various drawings indicate like elements.

DETAILED DESCRIPTION OF THE INVENTION

Figure 1:
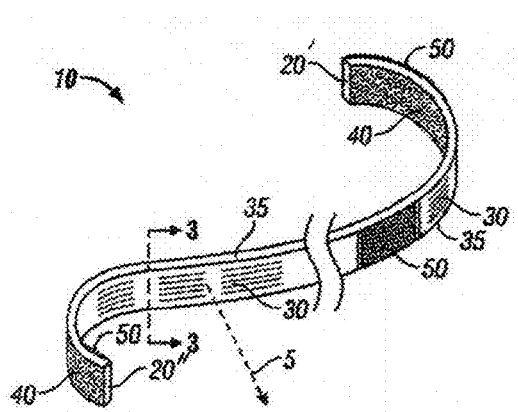
FIG. 1 is a perspective view of the presently described tourniquet band apparatus.

As discussed in the preceding summary and shown in FIG. 1, the presently described apparatus is a tourniquet band 10. The band 10 terminates at a pair of opposing free ends 20 and has a smooth finish surface 30 and an opposing fuzzy finish surface 40. The smooth and fuzzy finishes are a consequence of the type of threads that are used, and also of the type of weaving any post weaving steps, that are used in fabricating band 10 as will be described. Discrete patches 50 of hook type surface attachment material are bonded or otherwise attached to, and are a part of, band 10. One patch 50 may be bonded to each of the free ends 20, and one or more patches 50 may be bonded medially. The patches 50 are all attached to the smooth finish surface 30. The overall coverage of the hook type surface attachment material should leave open substantial regions of the band to allow bidirectional stretch of the band.

Figure 2:
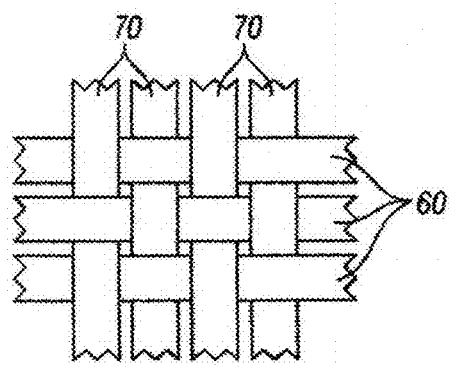
FIG. 2 is an enlarged plan view of a small portion of the band apparatus as seen along perspective line 5.

FIG. 2 shows the nature of the weave pattern of band 10 as seen from sight line 5 in FIG. 1. It is pointed out that longitudinal threads 60 extend in mutual parallel positions between the free ends 20, and that lateral threads 70 extend in mutual parallel positions between side edges 35 of band 10. The threads 60 are mutually orthogonal to threads 70.

Figure 3:
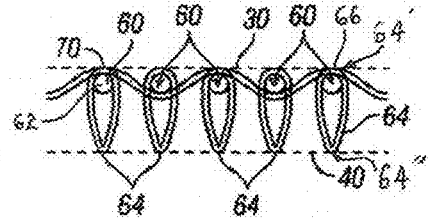
FIG. 3 is a cross-sectional view taken along line 3-3 in FIG. 1.

FIG. 3 is a typical cross section as viewed along the longitudinal threads 60 showing that the lateral threads 70 are woven alternately over and then under each next longitudinal thread 60 between the side edges 35. It is noted also that the threads 70 are pulled tight against threads 60. This enables threads 70 to be strong without taking up undue space so that the entire band 10 may be tightly woven.

Figure 4:
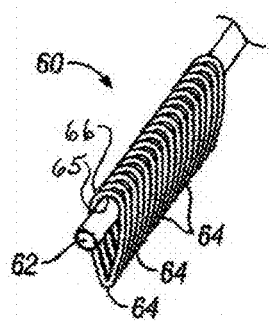
FIG. 4 is an enlarged view of a longitudinal thread of the band shown in FIG. 1.

FIGS. 3 and 4 shows details of one of the longitudinal threads 60. It is noted that a central elastic filament 62 is surrounded circumferentially by a densely-packed but loosely wound bundle of non-elastic closed loop filaments 64 where one end or side portion 64' of filaments 64 has loop inner surfaces 65 that are in intimate contact with filament 62 thereby forming the smooth finish surface 30 with the loop outer surfaces 66 corresponding to the loop inner surfaces contacting a partial circumferential portion of each longitudinal thread 60. The other end or side portion 64" of each filament 64 extends away from filament 62 as a closed loop thereby forming the fuzzy surface 40. This property is extremely important to the utility of band 10 in that it enables the fuzzy surface 40 to attach to receive any one of the patches 50. The loops are brought out from the interwoven fabric by applying a static charge to the band 10. Since all of the loops have the same charge polarity, they reject each other so that they tend to stand straight up and are able to be raked into a nap by a rotating roller having short fingers. This technique for developing a nap is disclosed in U.S. Pat. No. 658,539 to Baker and hereby incorporated herein by reference in its entirety. When band 10 experiences a longitudinal load or tension, filaments 62 elastically elongate developing a compressive pull-back which results in a hoop stress around the body part the band 10 is stretched around.

Figure 5:
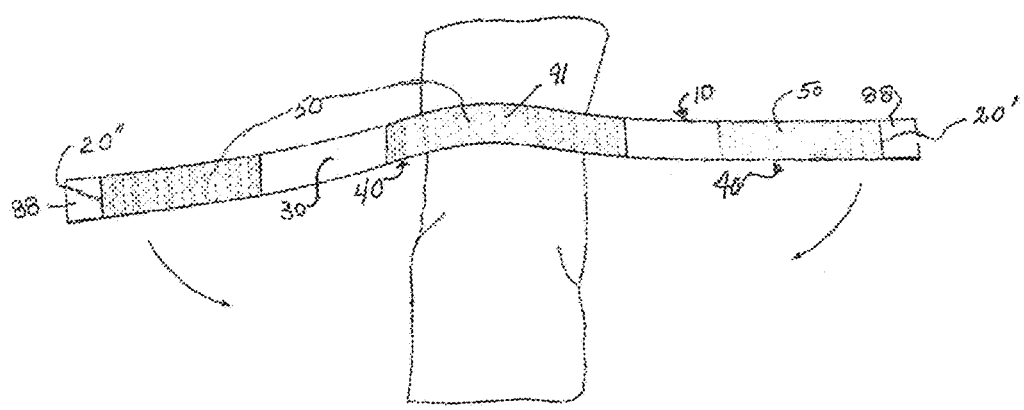
FIGS. 5, 6 and 7 are top views of the band as applied to a body part in a bi-directional manner for stemming blood flow.
Figure 6:
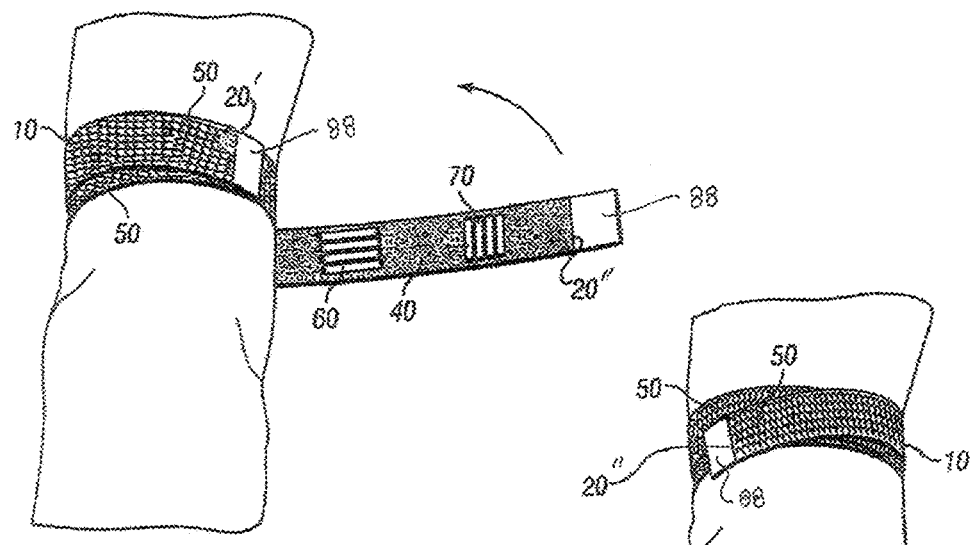
Figure 7:
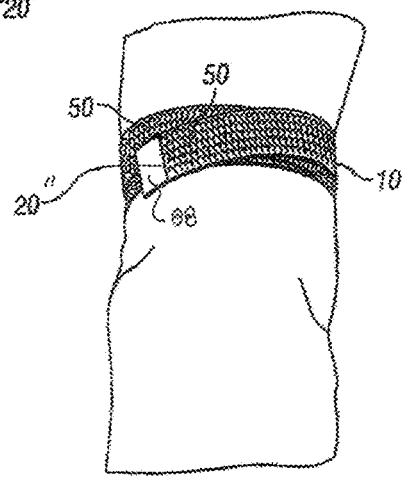

As shown in FIGS. 5, 6 and 7, pull tabs 88 can be supplied at the free ends 20' and 20", respectively, of the tourniquet. As also shown in these Figures, the bi-directional use of the band 10 is demonstrated. Because band 10 is longitudinally symmetrical it is clear that it may be applied to a body part starting at either of its free ends, referred to as the "start end." The end of the band 10 that is not used to start is referred to as the "terminal end." We also know that the same tourniquet forces will be applied to a body part if band 10 is coiled around the body part with either the smooth surface 30 or the fuzzy surface 40 facing the body part as band 10 is wrapped about it. For a large body part if band 10 is only able to circumvent once, any part of the patch 50 at the terminal end may be engaged with the outfacing fuzzy surface 40 so that any desired amount of compression may be achieved through a selective stretch of band 10. For a smaller limb, band 10 may further circumvent and any of the further patches 50 may be secured with the fuzzy surface so that even greater compressions may be achieved. No matter the size of the body part, one or more wraps may be coiled around it to achieve an exactly desired amount of compression. FIG. 6 also includes the representative threads 60 and 70 in partial cutaway view for directional reference.

Again, as shown in FIGS. 5, 6 and 7, band 10 is being applied in a bi-directional manner to a body part. By bi-directional is meant that the tourniquet band 10 is supplied with two free ends 20, and the band can be applied by placing the center 91 against the extremity and pulling the first free end 20' to secure it against the center, and then pulling the opposite free end 20" in the opposite direction, such as to secure the tourniquet over the extremity with resistive force from the elastic applied within the tourniquet in both directions. The tourniquet can be applied by medical personnel, such as a trained physician, nurse, or emergency technician, as well as an injured soldier, whether medically trained or a fellow soldier, in less than 30 seconds.

In one embodiment of the presently disclosed tourniquet band apparatus a flat, flexible and elongate length of fabric has a pair of longitudinally opposing free ends. The fabric has longitudinal threads extending in mutually parallel positions between the free ends, and woven into the longitudinal threads, lateral threads extending in mutually parallel positions at right angles to the longitudinal threads. Each of the longitudinal threads has a central elastic filament surrounded by a densely-packed but loosely wound bundle of non-elastic filaments. One side of each one of the bundle of non-elastic filaments is positioned in intimate contact with one central elastic filament, thereby forming the smooth surface of the length of fabric. A further side of each one of the bundle of non-elastic filaments is positioned as a loop extending away from said central elastic filament, thereby forming the fuzzy surface of the length of fabric. A patch of a hook-type attachment material is fastened to the smooth surface of the fabric wherein the patch is enabled for surface contact fastening with the fuzzy surface side of the fabric, whereby, the band is able to apply compression when coiled about a body part by elastically stretching the band and securing it in the stretched state by engaging at least one of the hook-type patches with the fuzzy surface. The lateral threads may be a serged-chain of non-elastic filaments. The longitudinally oriented threads are extensible by about 150% of their relaxed length. The band is able to exert a hoop stress of 5 psi for each layer of wrap. The central elastic filaments are made of one of polyurethane-polyurea copolymer, commonly known as Lycra or it may be made of natural rubber or other elastic materials.

The length of a tourniquet band may vary, and multiple tourniquets can be supplied for varying applications. Where the body part is an appendage such as an arm, desirable tourniquet dimensions are from about a minimum of 24 inches to a maximum of about 30 inches. For a leg, the dimensions are on the average order of about 30 inches minimum to a maximum of about 40 inches.

A tourniquet band can also be supplied in varying sizes, for instance in sizes of small, medium, large and extra large, having lengths of, respectively, for example, 28 inches, 32 inches, 36 inches and 38 inches. Larger sizes may be required, depending on the size and fitness of the intended populace. A pediatric version of the tourniquet band can be provided with smaller dimensions configured to be appropriate for children.

The tourniquet band can be supplied as part of emergency kits, particularly kits designed for vehicles, hiking, camping, household emergencies and the like. A disc may also be provided as part of such a kit, comprising a substantially flat, hard, non-compressible material. The disc provides a surface for contacting a body part, and connected to the band by having hook-type fastener applied to a surface opposite the surface contacting the body part.

Embodiments of the subject apparatus and method have been described herein. Nevertheless, it will be understood that various modifications may be made without departing from the spirit and understanding of this disclosure. Accordingly, other embodiments and approaches are within the scope of the following claims.

What is claimed is:

1. A compact tourniquet band for emergency hemorrhage control and tissue protection, comprising:
   a) a flat, flexible and elongate length of fabric having a pair of longitudinally opposing free ends;
   b) the fabric having longitudinal threads extending in mutually parallel positions between the free ends, and woven into the longitudinal threads, lateral threads extending in mutually parallel positions at right angles to the longitudinal threads;
   c) each of the longitudinal threads comprising:
      i) a central elastic extensible filament surrounded by a densely-packed bundle of non-elastic filaments, each of said non-elastic filaments configured as an elongate closed loop having a first end portion and a second end portion;
ii) the bundle of non-elastic filament elongate closed loops positioned so that a surface of each loop first end and second end portions form inner loop surfaces and outer loop surfaces, and said first end portion inner loop surface is in direct contact with a partial circumference portion of said central elastic filament where each said central elastic filament passes through the elongate closed loop formed by the said inner loop surface at the first end portion, wherein said first end portion outer loop surface corresponding to the length of the first end portion inner loop surface in contact with the partial circumference portion of the central elastic filament forms a portion of a smooth surface side of the length of fabric;
iii) said second end portion of each one of the bundle of non-elastic filament closed elongate loops extending away from said smooth surface side of the length of fabric thereby forming a fuzzy surface side of the length of fabric; and
d) at least one patch of a hook-type attachment material fastened to a portion of the smooth surface side of the fabric wherein the patch is enabled for surface contact fastening with a portion of the fuzzy surface side of the fabric; whereby, the band is able to apply emergency hemorrhage control and tissue protecting compression when coiled about a body part by elastically stretching the band and securing it in the stretched state by engaging at least one of said hook-type patches with at least one location on the fuzzy surface side of the length of fabric.

2. A compact tourniquet band for emergency hemorrhage control and tissue protection, comprising:
a) a flat, flexible and elongate length of fabric having a pair of longitudinally opposing free ends;
b) the fabric having longitudinal threads extending in mutually parallel positions between the free ends, and lateral threads connected to the longitudinal threads, said lateral threads extending in mutually parallel positions at about 90 degree angles to the longitudinal threads;
c) each of the longitudinal threads comprising:
i) a central elastic filament surrounded by a densely-packed but loosely wound bundle of non-elastic filaments, each of said non elastic-filaments configured as elongate closed loops each having a first end portion and a second end portion;
ii) the bundle of non-elastic filament elongate closed loops positioned so that a surface of each loop first end and second end portions form inner loop surfaces, and said first end portion inner loop surface is in direct partially-circumferential contact with one said central elastic filament, and each said central elastic filament passing through the elongate closed loop formed by the said inner loop surface at the first end portion, wherein said first end portion that is in direct contact with the central elastic filament has a corresponding loop outer surface that forms a portion of a smooth surface side of the length of fabric;
iii) said second end portion of each one of the bundle of non-elastic filament closed elongate loops extending away from said smooth surface side of the length of fabric thereby forming a fuzzy surface side of the length of fabric; and
d) at least one patch of a hook-type attachment material fastened to a portion of the smooth surface side of the fabric wherein the patch is enabled for surface contact fastening with a portion of the fuzzy surface side of the fabric; whereby, the band is constructed to apply emergency hemorrhage control and tissue protecting compression when coiled about a body part by elastically stretching the band and securing it in the stretched state by engaging at least one of said hook-type patches with at least one location on the fuzzy surface side of the length of fabric, said compression forming a hoop stress of at least about 5 psi for each layer of wrap around a body part.

3. A compact tourniquet band for emergency hemorrhage control and tissue protection, comprising:
a) a flat, flexible and elongate length of fabric having a pair of longitudinally opposing free ends;
b) the fabric having longitudinal threads extending in mutually parallel positions between the free ends, each of the longitudinal threads are elastically extensible up to about 150% of their relaxed length, and lateral threads connected to the longitudinal threads, said longitudinal threads and lateral threads being symmetrically configured so that a user of the tourniquet band may initiate use of the band from either opposing free end;
c) each of the longitudinal threads comprising:
i) a central elastic extensible filament surrounded by a densely-packed bundle of non-elastic filaments, each of said non-elastic filaments configured as an elongate closed loop having a first end portion and a second end portion;
ii) the bundle of non-elastic filament elongate closed loops positioned so that a surface of each loop first end and second end portions form inner loop surfaces and outer loop surfaces, and said first end portion inner loop surface is in contact with a partial circumference portion of said central elastic filament, and each said central elastic filament passing through the elongate closed loop formed by the said inner loop surface at the first end portion, wherein said first end portion outer loop surface corresponding to the length of the first end portion inner loop surface in contact with the partial circumference portion of the central elastic filament forms a portion of the smooth surface side of the length of fabric;
iii) said second end portion of each one of the bundle of non-elastic filament closed elongate loops extending away from said smooth surface side of the length of fabric thereby forming a fuzzy surface side of the length of fabric; and
d) at least one patch of a hook-type attachment material fastened to a portion of the smooth surface side of the fabric wherein the patch is enabled for surface contact fastening with a portion of the fuzzy surface side of the fabric; the band being constructed to apply emergency hemorrhage control and to mitigate any tourniquet-induced permanent tissue damage when coiled about a body part by elastically stretching the band and securing it in the stretched state by engaging at least one of said hook-type patches with at least one location on the fuzzy surface side of the length of fabric, said compression forming compression with a hoop stress of at least about 5 psi for each layer of wrap around a body part.

4. The tourniquet band of claim 3, in which said first end portion inner loop surface is in direct contact with a partial circumference of said central elastic filament, wherein the length of the contact by any one of said inner loop surfaces, measured axially along central elastic filament, is limited to the diameter of the non-elastic filament closed elongate loop in contact with the central elastic filament.

5. The tourniquet band of claim 3 comprising three hook-type patches symmetrically attached along the length of the band to enable either free end of the band to be placed at the site of a wound prior to wrapping the band.

6. The tourniquet band of claim 3 comprising at least three hook-type patches symmetrically attached along the length of the band to enable a patch located near the center of the band length to be placed at the site of a wound prior to bi-directional wrapping of the band free ends.

7. The tourniquet band of claim 3 in which the width of the band is about one and a half inches to two inches.

8. The tourniquet band of claim 3 in which the length of the band is twenty-eight inches.

9. The tourniquet band of claim 3 in which the length of the band is thirty-two inches.

10. The tourniquet band of claim 3 in which the length of the band is thirty-six inches.

11. The tourniquet band of claim 3 in which the length of the band is thirty-eight inches.

* * * * *